(12) United States Patent
Popplewell et al.

(10) Patent No.: US 12,324,452 B2
(45) Date of Patent: Jun. 10, 2025

(54) DELIVERY SYSTEMS AND METHODS OF PREPARING THE SAME

(71) Applicant: INTERNATIONAL FLAVORS & FRAGRANCES INC., New York, NY (US)

(72) Inventors: Lewis Michael Popplewell, Union Beach, NJ (US); Franklin Pringgosusanto, Union Beach, NJ (US); Lulu Henson, Union Beach, NJ (US)

(73) Assignee: INTERNATIONAL FLAVORS & FRAGRANCES INC., Newyork, NY (US)

( * ) Notice: Subject to any disclaimer, the term of this patent is extended or adjusted under 35 U.S.C. 154(b) by 528 days.

(21) Appl. No.: 17/219,021

(22) Filed: Mar. 31, 2021

(65) Prior Publication Data

US 2021/0212352 A1 Jul. 15, 2021

Related U.S. Application Data

(62) Division of application No. 15/568,813, filed as application No. PCT/US2016/029197 on Apr. 25, 2016, now Pat. No. 10,993,466.

(60) Provisional application No. 62/152,393, filed on Apr. 24, 2015.

(51) Int. Cl.
*A61K 8/81* (2006.01)
*A23L 27/00* (2016.01)
*A23P 20/25* (2016.01)
*A61K 8/02* (2006.01)
*A61K 8/25* (2006.01)
*A61K 8/85* (2006.01)
*A61K 8/92* (2006.01)
*A61Q 13/00* (2006.01)
*A61Q 15/00* (2006.01)
*B29C 64/112* (2017.01)
*B29C 64/209* (2017.01)
*B29C 64/295* (2017.01)
*B33Y 70/00* (2020.01)

(52) U.S. Cl.
CPC .............. *A23L 27/79* (2016.08); *A23L 27/70* (2016.08); *A23L 27/72* (2016.08); *A23P 20/25* (2016.08); *A61K 8/0233* (2013.01); *A61K 8/25* (2013.01); *A61K 8/8129* (2013.01); *A61K 8/85* (2013.01); *A61K 8/922* (2013.01); *A61Q 13/00* (2013.01); *A61Q 15/00* (2013.01); *B29C 64/112* (2017.08); *B29C 64/209* (2017.08); *B29C 64/295* (2017.08); *B33Y 70/00* (2014.12); *A23L 27/74* (2016.08); *A23L 27/75* (2016.08); *A23L 27/77* (2016.08); *A23P 2020/253* (2016.08); *A61K 2800/10* (2013.01)

(58) Field of Classification Search
CPC ... B29C 64/112; B29C 64/209; B29C 64/295; A61K 8/922; A61K 8/25; A61K 8/2129; A61K 8/85; A61K 8/0233; A23L 27/79; A23L 27/70; A23L 27/72; A23L 27/74
See application file for complete search history.

(56) References Cited

U.S. PATENT DOCUMENTS

| | | |
|---|---|---|
| 5,249,676 A | 10/1993 | Ashcraft et al. |
| 6,007,627 A | 12/1999 | Barnholtz |
| 6,892,639 B2 | 5/2005 | Compton et al. |
| 7,300,668 B2 | 11/2007 | Pryce Lewis et al. |
| 7,786,027 B2 | 8/2010 | Aquad et al. |
| 8,280,771 B2 | 10/2012 | Hendrickson et al. |
| 8,460,792 B2 | 6/2013 | Smets et al. |
| 8,522,711 B2 | 9/2013 | Mcneil et al. |
| 8,539,631 B2 | 9/2013 | Catalfamo et al. |
| 8,757,062 B2 | 6/2014 | Content et al. |
| 9,446,865 B2 | 9/2016 | Content et al. |
| 9,540,594 B2 | 1/2017 | Gonzales et al. |
| 9,969,154 B2 | 5/2018 | Content et al. |
| 9,988,595 B2 | 6/2018 | Brandt-Sanz et al. |
| 2003/0078552 A1 | 4/2003 | Tepper et al. |
| 2006/0038866 A1* | 2/2006 | Wen ................. C09D 11/30 106/31.89 |
| 2006/0147493 A1 | 7/2006 | Yang et al. |
| 2008/0014393 A1 | 1/2008 | Denome et al. |
| 2008/0041751 A1 | 2/2008 | Catalfamo et al. |
| 2009/0098192 A1 | 4/2009 | Fuisz |
| 2010/0047415 A1* | 2/2010 | Baydo .................. C09D 11/30 426/383 |
| 2010/0055264 A1* | 3/2010 | Liniger .................. A23P 20/11 426/303 |
| 2010/0303969 A1* | 12/2010 | Sengupta ................. A23F 5/14 131/354 |
| 2011/0014268 A1 | 1/2011 | Tsukioka et al. |
| 2011/0129924 A1 | 6/2011 | Ying et al. |
| 2013/0034633 A1 | 2/2013 | Von Hasseln et al. |

(Continued)

FOREIGN PATENT DOCUMENTS

EP 0802045 A1 10/1997

OTHER PUBLICATIONS

Communication pursuant to Articles 94(3) EPC dated Mar. 27, 2020; European Application No. 16784081.8, filed Oct. 23, 2017, 4 pages.
Extended European Search Report in European Patent Application EP 16784081, dated Nov. 6, 2018, 9 pages.
International Preliminary Report on Patentability in PCT/US2016/029197, dated Nov. 2, 2017.

(Continued)

*Primary Examiner* — Nahida Sultana

(57) ABSTRACT

Methods of preparing a delivery system are described. Each method uses a first and second printing materials. The second printing material contains an active material such as a fragrance, flavor, malodor counteracting agent, and mixture thereof.

3 Claims, No Drawings

(56) References Cited

U.S. PATENT DOCUMENTS

| | | | |
|---|---|---|---|
| 2014/0106032 A1* | 4/2014 | Dardelle | A61K 9/5089 |
| | | | 426/89 |
| 2014/0120229 A1 | 5/2014 | Allen et al. | |
| 2015/0051330 A1 | 2/2015 | Fang | |
| 2015/0059968 A1 | 3/2015 | Masayo et al. | |
| 2015/0104545 A1* | 4/2015 | Dardelle | A23L 2/56 |
| | | | 426/89 |
| 2015/0231825 A1* | 8/2015 | Swartz | B32B 1/00 |
| | | | 428/156 |
| 2015/0290926 A1 | 10/2015 | Branca et al. | |
| 2016/0106142 A1* | 4/2016 | Contractor | A23P 20/20 |
| | | | 99/516 |
| 2017/0165390 A1 | 6/2017 | Gruenbacher et al. | |
| 2017/0361496 A1 | 12/2017 | Schamp et al. | |
| 2018/0065310 A1 | 3/2018 | Hodgdon et al. | |
| 2018/0290157 A1 | 10/2018 | Gruenbacher et al. | |
| 2018/0296343 A1 | 10/2018 | Wei | |
| 2018/0334642 A1 | 11/2018 | Hodgdon et al. | |
| 2019/0202134 A1 | 7/2019 | Micic et al. | |
| 2019/0240124 A1* | 8/2019 | Dardelle | A61K 8/87 |
| 2020/0017265 A1* | 1/2020 | Loftis, Jr. | A23L 2/52 |
| 2020/0070245 A1 | 3/2020 | Fima et al. | |
| 2020/0190379 A1* | 6/2020 | Fefferman | C09K 5/063 |
| 2021/0106966 A1* | 4/2021 | Jerri | C11B 9/0003 |

OTHER PUBLICATIONS

International Search Report and Written Opinion in PCT/US2016/029197, dated Jul. 26, 2016.

Office Communication dated Oct. 27, 2020 from U.S. Appl. No. 15/568,813, filed Oct. 24, 2017.

\* cited by examiner

DELIVERY SYSTEMS AND METHODS OF PREPARING THE SAME

CROSS-REFERENCE TO RELATED APPLICATIONS

This application is a continuation of U.S. Ser. No. 15/568,813 filed Oct. 27, 2017, which is the U.S. National Phase of PCT/US2016/029197 filed Apr. 25, 2016 and claims priority to U.S. provisional application, Ser. No. 62/152,393 filed on Apr. 24, 2015, the contents of which are incorporated herein by reference in their entirety.

INTRODUCTION

A delivery system is useful to carry, apply, or release an active material to a target area in a time-delayed or controlled manner. Active materials include fragrances, flavors and malodor counteracting materials. They are often encapsulated in a polymeric wall or particle and can be released upon exposing to water, light, heat, or friction. See U.S. Pat. No. 7,745,386 and International Patent Application Publication WO 2014/011860.

Most encapsulation is achieved in emulsions, which require large-scale manufacturing equipment and plants. See U.S. Pat. No. 7,585,824 and US Application Publication 2014/0017287. Costly additional steps are required for preparation of delivery systems having a second coating. See US Patent Application 2010/0247660.

3D printing technology has been used to rapidly manufacture food products without the need of a large-scale plant. See U.S. Pat. No. 6,280,785 and US Patent Application Publication 2008/0260918. This technology has not yet been applied to design and fabricate fragrance or flavor delivery systems suitable for a variety of applications in consumer products.

There is a need to develop a cost-efficient and versatile method of preparing fragrance or flavor delivery systems.

SUMMARY

This invention is based on the unexpected discovery that delivery systems can be conveniently prepared using 3D printers with suitable printing materials.

One aspect of this invention relates to a method of preparing a delivery system. The method includes the steps of: (a) providing a first and second printing materials; (b) depositing the first printing material, the second printing material, or both to form a first thin layer; (c) repeating the depositing step a predetermined number of times (e.g., at least 5 times) so that a new thin layer is formed on top of a previously formed thin layer and a solid or semisolid layer-by-layer construction is thus prepared; and curing the construction, thereby preparing a delivery system. The first printing material contains a polymer having a melting point of 45° C. to 300° C., the second printing material contains an active material, and the active material is a fragrance, flavor, malodor counteracting agent, or combination thereof.

In some embodiments, each of the first and second printing materials is separately deposited via a printer head. As an illustration, the first printing material is deposited via a first printer head at a temperature of 100 to 300° C. and the second printing material is deposited via a second printer head at a temperature of 20 to 300° C.

Each of the first and second printing materials can contain a polymeric material having a melting point or glass transition point of 75 to 165° C. In some embodiments, the first printing material is porous or contains a water-dissoluble polymer. Examples include polyvinyl alcohol, polylactic acid, or a combination thereof. In other embodiments, the second printing material contains a fragranced polymer or a combination of a fragranced polymer and polylactic acid at a ratio of 1:9 to 9:1 (e.g., 40:60 to 90:10 and 50:50 to 75:25).

Also within the scope of this invention is another method of preparing a delivery system. The method includes the steps of: (a) providing a computer-readable three-dimensional model that defines the delivery system formed of a plurality of layers, at least one of which contains an active material; (b) depositing a first layer according to the computer-readable three-dimensional model by extruding a first printing material, a second printing material, or both through one or more printing heads; and (c) repeating step (b) a predetermined number of times (e.g., at least 5 times) to form a predetermined number of layers, each of which is bond to one or more layers adjacent to it, thereby preparing a delivery system containing an active material confined in one or more layers; each of the layers is porous or dissoluble; the first and second printing materials are compatible with each other; the second printing material contains an active material; and the active material is a fragrance, flavor, malodor counteracting agent, or mixture thereof.

The first and second printing materials are as described above and can be deposited in the way as described above.

Still within the scope of this invention is a third method of preparing a delivery system. The method includes the steps of: (a) providing a first film, (b) depositing an active material to one or more predetermined areas on the first film, e.g., through a printer head, (c) covering the active material and the first film with a second film, (d) bonding the first and second film thereby sealing the active material between the first and second films to obtain the delivery system, wherein each of the first and second films has a thickness of 1 to 100 micrometers (e.g., 10 to 100 micrometers, 5 to 50 micrometers and 10-40 micrometers), the active material, as a powder or oil, is a flavor, fragrance, malodor counteracting agent, or combination thereof.

Both the first and second films can be formed of an edible material (e.g., polyvinyl alcohol) and the active material is a flavor.

Another aspect of this invention relates to a computer-readable storage medium having data thereon representing a three-dimensional model suitable for use in manufacturing a delivery system, wherein the delivery system is formed of a printing material containing a substrate and an active material confined in the substrate, the substrate is porous or dissoluble, and the active material is a fragrance, flavor, malodor counteracting agent, or mixture thereof.

The substrate is formed of a polymeric material. The printing material can be any of the printing material described above.

The details of one or more embodiments of the invention are set forth in the description below. Other features, objects, and advantages of the invention will be apparent from the description and the claims.

DETAILED DESCRIPTION

It is unexpectedly found that fragrance delivery systems can be designed and accurately made to fit an application in a consumer product using a 3D printer with suitable polymers loaded with an active material.

In some embodiments, the delivery system is a multiple-layered sheet construction having a first outer layer, a second outer layer, a center layer between the first and second outer layer. Optionally, there are one or more additional layers between the center layer and the first outer layer or between the center layer and the second outer layer. The center layer and the optional additional layers constitute the inner layers. Each of the multiple layers (i.e., the first, second, center, and one or more additional layers) is in contact with the layer immediately next to it.

It is preferred that at least one of the multiple layers is different from the remaining layers in terms of thickness, porosity, polymeric material, active material, active material load, and/or diffusion rate.

As an illustration, the first outer layer, the second outer layer, the center layer, or the one or more additional layer contains a polymer that is breakable upon friction, contacting with water, changing of pH values, exposing to light (e.g., UV and visible) or being heated or cooled to a certain temperature (e.g., at or above 5° C., at or above 25° C., at or above 35° C., at or above 40° C., at or above 50° C., at or above 100° C., at or below 35° C., at or below 25° C., at or below 15° C., at or below 5° C., at or below 0° C., and at or below −5° C.).

In other embodiments, the delivery system has a multiple-layered cylindrical body including a cylindrical shell, a cylindrical core, and optionally one or more additional layers between the shell and core. The core can be hollow, which can further be filled with an active material (e.g., a fragrance oil).

Still in other embodiments, the delivery system has a spherical body including a core and a spherical outer layer coating the core. Optionally, there are one or more additional layers between the core and the outer layer. The core can be hollow, which can further be filled with an active material (e.g., a fragrance oil).

It is contemplated in this invention that the inner layers contains a high concentration of an active material, while the outer layers contains a relatively lower concentration of the active material. This construction enables the delivery system to last longer in its use life.

It is also contemplated that the inner layer contains an active material having a relatively lower vapor pressure as compared to that contained in the outer layers. The active material having a higher vapor pressure can release from the delivery system at a fast pace, thereby providing an immediate experience when a consumer product containing the delivery system is taken out of a package.

The active material can have a different diffusion rate in each layer, and thus overall release rate from the delivery system. Diffusion is the net movement of the active material from a region of high concentration to a region of low concentration, or from an inner layer to an outer layer and then to the environment. The release rate depends on the concentration gradient (e.g., the difference between the concentration of the inner layer and the outer layer), the porosity of the layers, the pore size in the layers, the thickness of the layers, and the molecular weight/vapor pressure of the active materials contained in the layers. In order to obtain a delivery system having a desired release rate, a skilled person in the art would be able design a system without undue experiment by choosing for each layer a suitable polymer, active material, thickness, the concentration of the active material.

The polymeric material used in the inner layers can be the same or different from the one used in the outer layers. If being different, they are typically compatible to each other, namely, they can bond to each other covalently or non-covalently. Optionally, an adhesive material is used to bond the multiple layers. Preferably, a layer is deposited onto another layer while both are at melted state. When both layers solidify, they bond to each other.

Non-covalent bonding includes (i) electrostatic interactions such as ionic interactions, hydrogen bonds, and halogen bonds; (ii) Van der Waals forces such as dipole-dipole interactions, dipole-induced dipole interactions, and London dispersion forces; (iii) π-effects such as π-π interactions, cation-π and anion-π interactions, and polar-π interactions; and (iv) hydrophobic effect, i.e., the desire for hydrophobic polymers and/or capsules to aggregate in an aqueous environment.

Polymers having multifunctional strong hydrogen bonding groups are suitable to be used in the adjacent layers to induce bonding. Polymers useful for preparing the delivery system can be positively or negatively charged, i.e., anionic or cationic polymers. A layer containing an anionic polymer can bond its adjacent layer that contains a cationic polymer. In case where both layers are positively charged, they are bonded using anions or negatively charged particles. On the other hand, if they are both negatively charged, the two layers are bonded using cations or positively charged particles.

Turning to covalent bonding, it includes ether bonds (—O—), ester bonds (—COO—); carbon-carbon single bonds, carbon-carbon double bonds, thioether bonds (—S—), disulfide bonds (—S—S—), thioester bonds (—CO—S—, —CS—O—, and —CSS—), amine bonds including secondary, tertiary and quaternary amines, imine bonds (—CR=N—, R being H or a substitute such as an aliphatic, heteroaliphatic, aryl, or heteroaryl group), hydroxylamine bonds (—O—NR—), amide bonds (—CONR—), urea bonds (—NR—CO—NR'—, R', independently from R, being H or a substitute such as an aliphatic, hetero-aliphatic, aryl, or heteroaryl group), carbamate bonds (—OCONR—), organic carbonate bonds (—OCOO—), sulfoxide bonds (—SO—), sulfonyl bonds (—SO$_2$—), sulfonamide bonds (—SO$_2$NR—), and organophosphate bonds. Crosslinkers can be used to bond adjacent layers covalently. Suitable crosslinkers are those having multiple functional groups, e.g., amine, hydroxyl, carboxyl, imine, nitrile, vinyl, aziridine, and epoxy.

For purposes of practicing this invention, the term "compatibility" refers to solubility/miscibility of the fragrance in the polymer and non-reactivity with the polymer. Compatibility can be ascertained using the following approaches:

(1) Hildebrand or Hansen solubility parameters (group additivity method) as set forth in Barton, "CRC Handbook of Polymer-Liquid interaction Parameters and Solubility Parameters", 1990 by CRC Press, Inc. ISBN 0-8493-3544-2 pp. 11-15;

(2) UNIFAC (Unified quasi chemical theory of liquid mixtures Functional-group Activity Coefficients "UFAC") methods which utilize a group additivity principle by using the groups to add a non-ideal part to Flory's theory of polymer solubility as set forth in Gmehling et al., "Vapor-Liquid Equilibria by UNIFAC Group Contribution. Revision and Extension. 2" Ind. Eng. Chem. Process. Des. Dev. 1982, 21, 118-27. Furthermore, this method is based on a statistical mechanical treatment derived from the quasi chemical lattice model. In addition, this method includes a combinatorial and a "free volume" contribution (UNIFAC-FV); and (3) Monte Carlo/molecular dynamics techniques as set forth in Jacobson, Solomon H. "Molecular Modeling Studies of Polymeric Transdermal Adhesives: Structure and Transport Mechanisms" Pharmaceutical Technology, September 1999, pp 120, 122, 124, 126, 128 and 130.

Method of Preparation

To prepare a delivery system, a 3D model is first provided, e.g., through a computer aided design program (CAD) such as AutoDesk, AutoCAD, SolidWorks, or Creo Parametric. The 3D model can also be generated via scanning a prototype model. The original design is then converted to an .STL (Standard Tessellation Language or STereo-Lithography) file, which stores the information for each surface of the 3D model in very small sections including their spatial coordinates (e.g., 1-100 µm).

The data stored in the .STL file is transferred to a 3D printer and is interpreted and converted to a printer-operable file (e.g., G-file), which divides the 3D .STL file into a sequence of two-dimensional (2D) cross sections (e.g., with a thickness of 25-100 µm). The printer, using the material fed to the one or more printer heads, constructs consecutive layers from a series of 2D layers derived from the original .STL file.

The above described process can be achieved on a 3D printing system including a computer, a printer server, a 3D printer device, and optional a switching device. The computer, print server, 3D printer, and switching device may be in communication and/or networked. One of ordinary skill in the art will recognize that the printing system can be configured and networked to include additional parts or omit one or more parts listed above.

The computer typically has a central processing device, viewing interface (e.g., a monitor or screen), input devices (e.g., keyboard and mouse), and software application for designing a computer-aided design ("CAD").

The computer may be in communication with a 3D printer device directly or through a print server. In some embodiments, a switching device is necessary between the computer, the printer server, and the printer device.

Each 3D printer device has one or more (e.g., two or more, three or more, and four or more) printer heads, which are optionally subjected to heating to a temperature of 50-300° C. and/or a pressure of 1.1-100 atmosphere (i.e., 101 KPa to 10,100 KPa) so that a printing material (e.g., a molten polymer) is successfully extruded from the printer heads. The heads can move to any desired spot within a predetermined 2D plane. The printer heads may also include, for example, a UV light producing mechanism for curing polymers.

Each 3D printer device also has a tray for receiving layers printed out of the heads. The tray can move up and down along a Z axis perpendicular to the 2D plane where the printer heads is operated.

The 3D printer device also may comprise a compartment for storing, pre-heating, and/or supplying printing materials such as fragranced polymers in the form of a filament or powder.

As an illustration, a delivery system is prepared following the procedure described below. A first outer layer (e.g., the first outer layer in a sheet-like delivery system) is formed of a first polymer, which is either loaded with an active material or free of an active material. The first polymer is formed by one of the following two routes: (i) extrusion of a molten polymer via a heated printer head at an elevated temperature, or (ii) polymerization of a polymer precursor and a curing/crosslinking agent followed by curing at a predetermined temperature (e.g., room temperature and elevated temperature).

In route (i), a polymer is heated to a flowable state (e.g., liquid and semi-solid), and subsequently extruded through a printer head under pressure. The polymer is allowed to solidify to form a layer before another layer of polymer is deposited on top of it.

In route (ii), a polymer precursor, either used directly or in a solvent, is dispersed onto a plate as a thin film through a printer head. The curing/crosslinking agent, also used directly or in a solvent, is added to the thin film of the polymer precursor to partially or completely polymerize the precursor so that a layer is formed. Optionally, an active material is added anytime in this step, e.g., as a mixture with the polymer precursor or with the curing/crosslinking agent, or being added separately through a printer head to a predetermined area of the thin film. After polymerization/curing, the active material is enclosed within the newly formed polymer.

Either in route (i) or (ii), the polymer is cured with the aid of heat, solvent, or UV light for a pre-determined period of time to achieve desirable properties, e.g., porosity, adhesion, compatibility, and durability.

After the formation of the first polymer layer, a second polymer layer is deposited on top of and bounds to the first polymer layer through route (i) or (ii). This deposition step can be repeated by a predetermined number of times (e.g., 1-100, 1-20, 1-10, 1-5, at least 2, at least 5, and at least 10 times). In a sheet-like delivery system, the last deposited layer becomes the second outer layer.

This same process can be used to prepare a ball-like or cylinder-like delivery system, in which the outer layer of the delivery system is prepared by layer-to-layer construction.

3D Printing Systems

Any 3D printer is suitable for preparing the delivery system of this invention. Examples are stereolithography systems (commercially available from 3D Systems), inkjet printing systems (commercially available from Z Corporation), selective laser sintering systems (commercially available from EOS GmbH), fused deposition modeling systems (commercially available from Stratasys), and laminate object manufacturing systems (commercially available from Cubic Technologies). Specialty 3D printers are designed for printing edibles from sugar, chocolate, candy, starch, and other food ingredients. These printers include ChefJet by 3D Systems, da Vinci series by XYZ printing, and Replicator 2X by Makerbot. The latter printer is a filament printer using molten polymers that come out of two extruders (i.e., printer heads) to create an object layer by layer. Technologies of these printers are described in U.S. Pat. Nos. 4,575,330; 3,683,212; 3,946,398; 4,938,816; 5,730,817; and 7,051,654.

In a stereolithography system, a thin layer of light-curable liquid resin is applied to a movable base. A light beam (e.g., UV) from a laser source is directed to a 2D cross section onto the base to polymerize the layer of resin. After solidification, to the solid layer is added another layer of liquid resin ready for curing by the UV beam. The thickness of the liquid resin layer is controlled and pre-determined. This process is repeated, layer by layer, until the delivery system is completed. The active material is compatible with the liquid resin and the UV beam. It can be pre-mixed with the resin curing or added separately to the layer before curing.

In an inkjet system, ink droplets are delivered to a 2D cross section according to the .STL file stored in the computer, which is a part of the printing system. The droplet size and spacing are predetermined and controlled by the computer and printer unit. The inkjet system can handle both liquid- and solid-based material. Solid particles, typically having a particle size of 1-200 μm (e.g., 20-100 μm and 50-100 μm), are extruded from a printer head to form a pre-determined layer and bonded by a liquid adhesive. Both the solid particles and the liquid adhesives can be loaded with an active material. Alternatively, the active material is added to the layer before bonding. Exemplary solid particles are fragranced polymers such as PolyIFF described below. Other suitable particles include fragranced or unfragranced ceramic, glass, clay, and metal materials.

In a selective laser sintering system, a layer of a light-curable polymeric powder is dispersed to a base. A high power laser beam is directed to a 2D cross section on the base to locally fuse the polymeric powder so that they are bound together. After solidification, another layer of a polymeric powder is added on top of the fused layer. This process is repeated until the delivery system is completed. The powders that are not sintered are removed at the end of the process. Suitable light-curable polymers are those loaded with an active material (e.g., a fragrance) or free of the active material. An active material can also be added to the layer of polymer powders in the form of a liquid or solid.

In a fused deposition modeling system, a thermoplastic polymer is melted at an elevated temperature and then extruded through a heated printer head to a base according to the .STL file. The process is repeated to deposit additional layers. Different materials can be readily used in the each layer. Typically, the thermoplastic polymer is a fragranced polymer described below. Replicator 2×, a printer mentioned above and used in examples below is a fused deposition modeling system.

In a laminated object manufacturing system, a sheet material is placed on a base. A laser or razor is used to carve out a 2D cross section to prepare the first layer. Another sheet material is placed on top of the first layer and subsequently carved out. The process is repeated. Adjacent layers are bonded by use of adhesive or welding.

Polymeric Materials for 3D Printing

Described below are suitable materials for preparing the delivery system including the outer layers, the inner layers, shells, and cores.

Suitable polymers include polylactic acid (PLA, printing temperature 180-230° C.), acrylonitrile butadiene styrene (ABS, printing temperature 110-230° C.), conductive ABS (modified ABS having a resistance of 1200 ohm/cm or less; commercially available from MakerGeeks, Missouri, USA; printing temperature 200-230° C.), polyvinyl acetate (PVA, printing temperature 160-175° C.), a wood-filled filament (e.g., LAYWOO-D3, commercially available from Orbi-Tech, Leichlingen, Nordrhein Westfalen, Germany; a wood-like material; printing temperature 175-250° C.), a sandstone/ceramic/chalk-filled filament (e.g., LAYBRICK commercially available from Orbi-Tech; a sandstone-like material; printing temperature 180-200° C.), Nylon (e.g., Taulman 618, commercially available from Taulman 3D, Missouri, USA; printing temperature 240-250° C.), modified butadiene (e.g., Bendlay commercially available from Orbi-tech; clear and adhesive suitable for interlayer bonding; printing temperature 230-240° C.), polycarbonate (a tough and durable thermoplastic material; printing temperature 255-300° C.), high impact polystyrene (HIPS, printing temperature 220-230° C.).

Friable polymers break and then release active materials loaded in or covered by these polymers. Examples include those described in US 2006/0287440 such as macrocyclic poly(1,4-butylene terephthalate) (PBT), poly(1,3-propylene terephthalate) (PPT), poly(1,4-cyclohexylenedimethylene terephthalate) (PCT), poly(ethylene terephthalate) (PET), and poly(1,2-ethylene 2,6-naphthalenedicarboxylate) (PEN) oligomers, copolyester oligomers comprising two or more of the above monomer repeat units, poly(vinyl butyral-co-vinyl alcohol-co-vinyl acetate), poly(butyl methacrylate co-methyl methacrylate), poly[butylene terephthalate-co-poly(alkylene glycol) terephthalate], and poly(ethyl methacrylate co-glycidyl methacrylate. Additional suitable polymers are polyurea, polyurethane, sol-gel, hydrogel, aminoplasts, gelatin, urea-formaldehyde, melamine-formaldehyde, and polyester. See US 2011/0071064, U.S. Pat. Nos. 3,894,979, and 3,585,259.

Water degradable polymers break apart, partially or fully dissolve or disperse in water when the delivery system is in contact with water including moisture. Examples include polyethylene oxide, copolymers of polyethylene oxide and polypropylene oxide, other water dispersible ethylene oxide copolymers, water dispersible blends of polyethylene oxide, water degradable grades of polyvinyl alcohol, blends of polyvinyl alcohol, polyethyloxazoline, water degradable branched polyesters and copolyesters, water dispersible polyurethanes, water degradable acrylic acid based copolymers, water dispersible polyvinyl methyl ether, cellulose derivatives such as methyl cellulose, hydroxypropyl cellulose, methylated hydroxypropyl cellulose, hydroxypropyl methyl cellulose, water degradable vinyl polymers, water degradable copolymers of lactic acid and a modifying monomer selected from the group consisting of ethylene glycols, polyethylene glycols, propylene glycols, polypropylene glycols, P-dioxanone, 1,5-dioxepan-2-one, 1,4-oxathialan-2-one, 1,4-dioxide, and mixtures thereof, and the like. See U.S. Pat. Nos. 6,117,438, 8,772,205, and 5,360,892.

Light sensitive polymers degrade upon exposure to light (e.g., UV). U.S. Pat. No. 5,360,892 describes UV degradable polylactic acid copolymers mentioned immediately above. CA 1,054,287 teaches light degradable polymers that are copolymers of polyethylene, polypropylene, and ethylene-vinylacetate, each containing an olefinically unsaturated moiety (e.g., 1,6-diphenylhexatriene and 5-phenyl-1,3-pentadiene). More suitable light sensitive polymers can be found in WO 2013/169953 such as polymers prepared containing 4,5-dimethoxy-2-nitrobenzyl moiety.

Examples of heat sensitive polymers are those described in U.S. Pat. Nos. 5,025,266, 6,103,528, 7,051,654, and WO 2003/106536, e.g., polymers having conjugated polyenes and sulfonic acid groups, copolymers of polyethylene oxide and polypropylene oxide. Additional examples include polystyrene, polyethylene, polymethylmethacrylate, polypropylene, poly(N-isopropylacrylamide), hydroxypropylcellulose, poly(vinylcaprolactame), polyvinyl methyl ether, polyethylene oxide, polyvinylmethylether, polyhydroxyethylmethacrylate, polyacrylic acid, poly(N-acryloylglycinamide), ureido-functionalized polymers, copolymers from N-vinylimidazole and 1-vinyl-2-(hydroxylmethyl) imidazole, and copolymers from acrylamide and acrylonitrile.

In addition to the polymers described above, porous polymers can also be used to form the first or second outer layer. These polymers include polyethersulfone, polysulfone, polyacrylonitrile, polyetherimide, polyamide-imide, cellulose acetate, poly(phenylene oxide), sulfonated polyethersulfone, sulfonated polysulfone, polybenzimidazole, polyvinyl alcohol, and sulfonated poly(phenylene oxide).

Food grade printing materials are also contemplated. Examples are sugars, sugar derivatives, modified starches, proteins, alcohols, celluloses, dextrins, gums, sugar polyols, peptides, acids, carbohydrates, hydrocolloids. Particular examples of suitable materials include sugars such as sucrose, glucose, lactose, levulose, trehalose, fructose, maltose, ribose, dextrose, isomalt, sorbitol, mannitol, xylitol, lactitol, maltitol, pentatol, arabinose, pentose, xylose, galactose; hydrogenated starch hydrolysates, inulin, oligosaccharides such as oligofructose; maltodextrins or dextrins (i.e., soluble fiber); hydrocolloids such as agar, gum acacia, modified gum acacia, sodium alginate, potassium alginate, ammonium alginate, calcium alginate or carrageenan; gums; polydextrose; celluloses such as sodium carboxymethylcellulose, enzymatically hydrolyzed carboxy methyl cellulose, methyl cellulose, hydroxypropyl cellulose and hydroxypropyl methyl cellulose; proteins such as gelatin, pea protein, soy and whey protein isolates and hydrolyzates, and sodium caseinates; and derivatives and mixtures thereof.

Either the first or second outer layers can be free of an active material or loaded with an active material. When one of them is free of an active material, it is preferably formed of polymers that are either porous or breakable (e.g., degradable) so that the active material contained in the one or more inner layers releases from the delivery system. On the other hand, when the first or second outer layer is loaded with an active material, it is formed of a porous polymer. The active material contained in the one or more inner layers releases from the delivery system through the pores of the first or second outer layer. The active material contained in each of the layers can be the same or different. Each of the layers can contain the same or different concentration of the active material as each other. In a preferred embodiment, the inner layers each contain a higher concentration of an active material than the outer layers. In another preferred embodiment, the inner layers each contain an active material having a higher vapor pressure than that contained in the outer layers.

Polymers loaded with an active material are described in U.S. Pat. Nos. 4,247,498; 4,428,869; 4,521,541; 6,207,514; 6,213,409, 6,500,444; and 7,105,064.

Examples included fragranced polymers such as POLYIFF® polymers (commercially available from IFF, Union Beach, NJ, USA). These polymers typically contain olefinic polymers (e.g., polyethylene or polypropylene) and fragrance. As shown in the above US patents, POLYIFF® can be manufactured by an extrusion process during which fragrance or flavor oil is introduced to the molten polymer in the extruder via an injection port using a pump.

Methods of preparing fragranced polymers can also be found in U.S. Pat. No. 3,505,432. The methods include the steps of: (a) mixing a first amount of liquid with a relatively large amount of scent-imparting material to form a flowable mass; (b) forming drops from said mass and causing substantially instantaneous solidification of said drops into polyolefin pellets having a relatively large amount of scent-imparting material imprisoned therein; (c) melting said pellets with a second amount of said polyolefin, said second amount being larger than said first amount; and (d) solidifying the melt of (c).).

Additional polymers are microporous thermoplastic polymers described in U.S. Pat. No. 4,247,498, which are capable of containing fragrance or flavor. These polymers include olefinic (both non-acrylic and acrylic) polymers, condensations polymers, and oxidation polymers. Exemplary of the useful non-acrylic polyolefins are low density polyethylene, high density polyethylene, polypropylene, polystyrene, polyvinylchloride, acrylonitrile-butadiene-styrene terpolymers, styrene-acrylonitrile copolymer, styrene butadiene copolymers, poly(4-methyl-pentene-1), polybutylene, polyvinylidene chloride, polyvinyl butyral, chlorinated polyethylene, ethylene-vinyl acetate copolymers, polyvinyl acetate, and polyvinyl alcohol. Useful acrylic polyolefins include polymethyl-methacrylate, polymethyl-acrylate, ethylene-acrylic acid copolymers, and ethylene-acrylic acid metal salt copolymers. Polyphenylene oxide is representative of the oxidation polymers. Useful condensation polymers include polyethylene terephthalate, polybutylene terephthalate, Nylon 6, Nylon 11, Nylon 13, Nylon 66, polycarbonates and polysulfones.

Fragranced polyurethane is another polymer suitable for use in this invention. These polymers can be prepared by the reaction of one or more diols and a urethane precursor. Exemplary diols include alkylene diols (e.g., ethylene glycol, diethylene glycol, and propylene glycols), long chain polyoxyalkylene diols, linear polyester diols derived from the condensation of one or more diols with one or more dibasic acids, and the reaction product of one or more alkylene diols with a difunctional linear polyester derived from the condensation of one or more diols with one or more dibasic acids. The urethane precursor can be a polyisocyanate, a nitrile carbonate, or a polyfunctional lactone having the formula

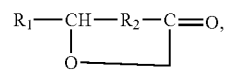

wherein $R_1$ is a monovalent radical selected from the group consisting of H, —$CHNH_2$, —$SO_2CH_3$, —CHOHCOOH, and —$(CHOH)_nCH_2OH$; n being an integer from 0 to 5; and $R_2$ is a divalent radical —$(CHOH)_m$—; m being an integer from 2 to 10; and ethers derived from said lactones. U.S. Pat. No. 4,156,067 discloses polyurethane polymers characterized by a molecular weight of above 6,000 and having lactone groups and hydroxyl groups in the polymer backbone being prepared by reacting a mixture of polyols, a polyfunctional lactone (e.g., epsilon caprolactone) and a polyfunctional isocyanate proportioned so as to provide certain desired polymer properties for slow release of fragrance contained therein.

Polymeric particles disclosed in U.S. Pat. No. 7,105,064 are also useful. They can contain a fragrance or malodor counteractive agent. The polymeric particles have infrastructures composed of ethylene-vinyl copolymers, polymethyl methacrylate, polystyrene and/or ethylcellulose.

Any of the above-described polymeric materials can further contain a filler which creates a diffusion barrier, and/or increases the impact resistance and the modulus of elasticity. Examples of such fillers are $SiO_2$, $CaCO_3$, $MgCO_3$, $Al_2O_3$, MgO, ZnO, $TiO_2$, surface-modified silicas, zeolites (hydrated alkali metal-aluminum silicates), clays, modified clays, wood flour, gypsum ($CaSO_4·2H_2O$) and activated carbon. The polymeric materials can also contain a solvent, for example, one or more of isopropyl myristate, diethyl phthalate, dibutyl phthalate, diisopropyl adipate, benzyl benzoate, mineral oil, a methyl ester of a vegetable-derived $C_{12}$-$C_{18}$ carboxylic acid, for example, "soybean methyl ester", the methyl ester of a mixture of oleic acid, linleic acid, linolenic acid and saturated fatty acids, and a glyceryl ester of a vegetable-derived $C_{10}$ carboxylic acid, preferably the triglyceride of a mixture of caprylic acid and capric acid marketed under the trademark, NEOBEE-M5 (Stepan Chemical Company, Northfield, Ill.).

It is contemplated in this invention that the inner layers contains a high concentration of an active material, while the outer layers contains a relatively lower concentration of the active material. This construction enables the delivery system to last longer in its use life.

It is also contemplated that the inner layer contains an active material having a relatively lower vapor pressure as compared to that contained in the outer layers. The active material having a higher vapor pressure can release from the delivery system at a greater rate and a fast pace, thereby providing an immediate experience when a consumer takes the delivery system out of a package.

The active material can have a different diffusion rate in each layer. Diffusion is the net movement of the active material from a region of high concentration to a region of low concentration, or from an inner layer to an outer layer and then to the environment.

The polymeric material used in the inner layers can be the same or different from the one used in the outer layers. If being different, they are typically compatible to each other, namely, they can bond to each other covalently or non-covalently. Optionally, an adhesive material is used to bond the multiple layers. Preferably, a layer is deposited onto another layer while both are at melted state. When both layers solidify, they bond to each other.

For purposes of practicing our invention, "compatibility" which is a measure of solubility/miscibility and non-reactivity of the fragrance and the polymer is ascertained herein using the following approaches:
  (1) Hildebrand or Hansen solubility parameters (group additivity method) as set forth in Barton, "CRC Handbook of Polymer-Liquid interaction Parameters and Solubility Parameters", 1990 by CRC Press, Inc. ISBN 0-8493-3544-2 pp. 11-15;
  (2) UNIFAC (Unified quasi chemical theory of liquid mixtures Functional-group Activity Coefficients "UFAC") methods which utilize a group additivity principle by using the groups to add a non-ideal part to Flory's theory of polymer solubility as set forth in Gmehling et al., "Vapor-Liquid Equilibria by UNIFAC Group Contribution. Revision and Extension. 2" Ind. Eng. Chem. Process. Des. Dev. 1982, 21, 118-27. Furthermore, this method is based on a statistical mechanical treatment derived from the quasi chemical lattice model. In addition, this method includes a combinatorial and a "free volume" contribution (UNIFAC-FV); and
  (3) Monte Carlo/molecular dynamics techniques as set forth in Jacobson, Solomon H. "Molecular Modeling Studies of Polymeric Transdermal Adhesives: Structure and Transport Mechanisms" Pharmaceutical Technology, September 1999, pp 120, 122, 124, 126, 128 and 130.

Other Delivery Systems

The delivery system of this invention can be formulated into a composition containing one or more additional delivery systems (e.g., microcapsules).

Encapsulation of active material such as fragrances is known in the art, see for example U.S. Pat. Nos. 2,800,457, 3,870,542, 3,516,941, 3,415,758, 3,041,288, 5,112,688, 6,329,057, and 6,261,483. Preferred encapsulating polymers include those formed from, acrylates, acrylamide, acrylate-co-acrylamide, melamine-formaldehyde or urea-formaldehyde condensates, as well as similar types of aminoplasts. Other wall forming materials include, polysiloxanes, polyamide, polyimide, polyvinyl alcohol, polyanhydride, polyolefin, polysulfone, polysaccharide, protein, polylactide (PLA), polyglycolide (PGA), polyorthoester, polyphosphazene, silicone, lipid, modified cellulose, gums, polystyrene, and polyesters or combinations of these materials. Other polymeric materials that are functional are ethylene maleic anyhydride copolymer, styrene maleic anhydride copolymer, ethylene vinyl acetate copolymer, and lactide glycolide copolymer. Bio-polymers that are derived from alginate, chitosan, collegen, dextran, gelatin, and starch can also be used as the encapsulating materials. Additionally, microcapsules can be made via the simple or complex coacervation of gelatin.

In addition to microcapsules, suitable delivery systems include polymer-assisted delivery compositions (see U.S. Pat. No. 8,187,580), fiber-assisted delivery compositions (US 2010/0305021), cyclodextrin host guest complexes (U.S. Pat. No. 6,287,603 and US 2002/0019369), pro-fragrances (WO 2000/072816 and EP 0 922 084), and any combination thereof. Additional examples include (i) polymer matrix delivery systems such as melt extruded flavor/fragrance and spray dry encapsulation; (ii) single wall capsules such as aminoplasts, hydrogel, sol-gel, coascervate capsules, polyurea/polyurethane capsules, and melamine formaldehyde capsules; (iii) cyclodextrin delivery system; (iv) pro-perfume including reaction products of a primary/secondary amine, aromatic or non-aromatic imines (Schiff bases), oxazolidines, beta-keto esters, orthoesters, compounds comprising one or more beta-oxy or beta-thio carbonyl moieties capable of releasing a perfume (e.g., an alpha, beta-unsaturated ketone, aldehyde or carboxylic ester).

Active Materials.

Active materials contained in the delivery system can include one or more the following materials: flavors, fragrance ingredients such as fragrance oils, taste masking agents, taste sensates, malodor counteractants (i.e., malodor counteractive agents and malodor control agents), vitamins, dyes, colorants, pigments, anti-inflammatory agents, anesthetics, analgesics, antifungal agents, antibiotics, anti-viral agents, anti-parasitic agents, anti-infectious/anti-acne agents, dermatological active ingredients, enzymes and co-enzymes, skin whitening agents, anti-histamines, chemotherapeutic agents, insect repellents, sunscreen actives, core modifiers, and sacrificial core ingredients.

Nonlimiting examples of perfumes include those described in WO2015/023961. The delivery system can also include the following active materials:
  (i) taste masking agents, substances for masking one or more unpleasant taste sensations, in particular a bitter, astringent and/or metallic taste sensation or aftertaste. Examples include lactisol [2O-(4-methoxyphenyl) lactic acid] (cf. U.S. Pat. No. 5,045,336), 2,4-dihydroxybenzoic acid potassium salt (cf. U.S. Pat. No. 5,643,941), ginger extracts (cf. GB 2,380,936), neohesperidine dihydrochalcone (cf. Manufacturing Chemist 2000 July issue, p. 16-17), specific flavones (2-phenylchrom-2-en-4-ones) (cf. U.S. Pat. No. 5,580,545), specific nucleotides, for example cytidine-5'-monophosphates (CMP) (cf. US 2002/0177576), specific sodium salts, such as sodium chloride, sodium citrate, sodium acetate and sodium lactate (cf. Nature, 1997, Vol. 387, p. 563), a lipoprotein of .beta.-lactoglobulin and phosphatidic acid (cf. EPA 635 218), neodiosmine [5,7-dihydroxy-2-(4-methoxy-3-hydroxyphenyl)-7-O-neohesperidosyl-chrom-2-en-4-one] (cf. U.S. Pat. No. 4,154,862), preferably hydroxyflavanones according to EP 1 258 200, in turn preferred in this respect 2-(4-hydroxyphenyl)-5,7-dihydroxychroman-4-one (naringenin), 2-(3,4-dihydroxyphenyl)-5,7-dihydroxychroman-4-one (eriodictyol), 2-(3,4-dihydroxyphenyl)-5-hydroxy-7-methoxychroman-4-one (eriodictyol-7-methylether), 2-(3,4-dihydroxyphenyl)-7-hydroxy-5-methoxychroman-4-one (eriodictyol-5-methylether) and 2-(4-hydroxy-3-methoxyphenyl)-5,7-dihydroxychroman-4-one (homoeriodictyol), the (2S)- or (2R)-enantiomers thereof or mixtures thereof as well as the mono- or polyvalent phenolate salts thereof with $Na^+$, $K^+$, $NH^{4+}$, $Ca^{2+}$, $Mg^{2+}$ or $Al^{3+}$ as counter cations or .gamma.-aminobutyric acid (4-aminobutyric acid, as the neutral form ("inner salt") or in the carboxylate or ammonium form) according to WO 2005/09684;

(ii) taste sensates including hot tasting, salivation-inducing substances, substances causing a warmth or tingling feeling, and cooling active ingredients. Examples of hot tasting and/or salivation-inducing substances and/or substances which cause a feeling of warmth and/or a tingling feeling on the skin or on the mucous membranes and which can be a constituent of the products according to the invention are: capsaicin, dihydrocapsaicin, gingerol, paradol, shogaol, piperine, carboxylic acid-N-vanillylamides, in particular nonanoic acid-N-vanillylamide, pellitorin or spilanthol, 2-nonanoic acid amides, in particular 2-nonanoic acid-N-isobutylamide, 2-nonanoic acid-N-4-hydroxy-3-methoxyphenylamide, alkyl ethers of 4-hydroxy-3-methoxybenzyl alcohol, in particular 4-hydroxy-3-methoxybenzyl-n-butylether, alkyl ethers of 4-acyloxy-3-methoxybenzyl alcohol, in particular 4-acetyloxy-3-methoxybenzyl-n-butylether and 4-acetyloxy-3-methoxybenzyl-n-hexylether, alkyl ethers of 3-hydroxy-4-methoxybenzyl alcohol, alkyl ethers of 3,4-dimethoxybenzyl alcohol, alkyl ethers of 3-ethoxy-4-hydroxybenzyl alcohol, alkyl ethers of 3,4-methylene dioxybenzyl alcohol, (4-hydroxy-3-methoxyphenyl) acetic acid amides, in particular (4-hydroxy-3-methoxyphenyl) acetic acid-N-n-octylamide, vanillomandelic acid alkylamides, ferulic acid-phenethylamides, nicotinaldehyde, methylnicotinate, propylnicotinate, 2-butoxyethylnicotinate, benzylnicotinate, 1-acetoxychavicol, polygodial and isodrimeninol, further preferred cis- and/or trans-pellitorin according to WO 2004/000787 or WO 2004/043906, alkenecarboxylic acid-N-alkylamides according to WO 2005/044778, mandelic acid alkylamides according to WO 03/106404 or alkyloxyalkanoic acid amides according to WO 2006/003210. Examples of preferred hot tasting natural extracts and/or natural extracts which cause a feeling of warmth and/or a tingling feeling on the skin or on the mucous membranes and which can be a constituent of the products according to the invention are: extracts of paprika, extracts of pepper (for example *capsicum* extract), extracts of chili pepper, extracts of ginger roots, extracts of Aframomum melgueta, extracts of Spilanthes-*acmella*, extracts of Kaempferia galangal or extracts of Alpinia galanga. Suitable cooling active ingredients include the following: 1-menthol, d-menthol, racemic menthol, menthone glycerol acetal (trade name: Frescolat®MGA), menthyl lactate (trade name: Frescolat®ML, menthyl lactate preferably being 1-menthyl lactate, in particular 1-menthyl-1-lactate), substituted menthyl-3-carboxamides (for example menthyl-3-carboxylic acid-N-ethylamide), 2-isopropyl-N-2,3-trimethyl-butanamide, substituted cyclohexane carboxamides, 3-menthoxypropane-1,2-diol, 2-hydroxyethyl menthyl carbonate, 2-hydroxypropyl menthyl carbonate, N-acetylglycine menthyl ester, isopulegol, hydroxycarboxylic acid menthyl esters (for example menthyl-3-hydroxybutyrate), monomenthyl succinate, 2-mercaptocyclodecanone, menthyl-2-pyrrolidin-5-onecarboxylate, 2,3-dihydroxy-p-menthane, 3,3,5-trimethylcyclohexanone glycerol ketal, 3-menthyl-3,6-di- and -trioxaalkanoates, 3-menthyl methoxyacetate and icilin. Cooling active ingredients which are particularly preferred are as follows: 1-menthol, racemic menthol, menthone glycerol acetal (trade name: Frescolat®MGA), menthyl lactate (preferably 1-menthyl lactate, in particular 1-menthyl-1-lactate, trade name: Frescolat®ML), 3-menthoxypropane-1,2-diol, 2-hydroxyethyl menthyl carbonate, 2-hydroxypropyl menthyl carbonate.

(iii) malodor counteracting agents including an α,β-unsaturated carbonyl compounds including but not limited to those disclosed in U.S. Pat. No. 6,610,648 and EP 2,524,704, amyl cinnamaldehyde, benzophenone, benzyl benzoate, benzyl isoeugenol, benzyl phenyl acetate, benzyl salicylate, butyl cinnamate, cinnamyl butyrate, cinnamyl isovalerate, cinnamyl propionate, decyl acetate, ethyl myristate, isobutyl cinnamate, isoamyl salicylate, phenethyl benzoate, phenethyl phenyl acetate, triethyl citrate, tripropylene glycol n-butyl ether, isomers of bicyclo[2.2.1]hept-5-ene-2-carboxylic acid, ethyl ester, nano silver, zinc undecenylate, β-naphthyl methyl ether, β-naphthyl ketone, benzyl acetone. They may include mixture of hexahydro-4,7-methanoinden-5-yl propionate and hexahydro-4,7-methanoinden-6-yl propionate; 4-(2,6,6-trimethyl-2-cyclohexen-1-yl)-3-methyl-3-buten-2-one; 3,7-dimethyl-2,6-nonadien-1-nitrile; dodecahydro-3a,6,6,9a-tetramethylnaphtho (2,1-b) furan; ethylene glycol cyclic ester of n-dodecanedioic acid; 1-cyclohexadecen-6-one; 1-cycloheptadecen-10-one; and corn mint oil. They may also include 1-cyclohexylethan-1-yl butyrate; 1-cyclohexylethan-1-yl acetate; 1-cyclohexylethan-1-ol; 1-(4'-methylethyl)cyclohexylethan-1-yl propionate; and 2'-hydroxy-1'-ethyl(2-phenoxy)acetate each of which compound is marketed under the trademark VEILEX by International Flavors & Fragrances Inc. More suitable malodor counteracting agents are polymers containing an α-keto, benzaldehyde, or α,β-unsaturated carbonyl moiety, such as those described in US Application Publications 2012/0294821, 2013/0101544 and 2013/0101545;

(iv) vitamins including any vitamin, a derivative thereof and a salt thereof. Examples are as follows: vitamin A and its analogs and derivatives (e.g., retinol, retinal, retinyl palmitate, retinoic acid, tretinoin, and isotretinoin, known collectively as retinoids), vitamin E (tocopherol and its derivatives), vitamin C (L-ascorbic acid and its esters and other derivatives), vitamin B3 (niacinamide and its derivatives), alpha hydroxy acids (such as glycolic acid, lactic acid, tartaric acid, malic acid, citric acid, etc.) and beta hydroxy acids (such as salicylic acid and the like);

(v) antibacterials including bisguanidines (e.g., chlorhexidine digluconate), diphenyl compounds, benzyl alcohols, trihalocarbanilides, quaternary ammonium compounds, ethoxylated phenols, and phenolic compounds, such as halo-substituted phenolic compounds, like PCMX (i.e., p-chloro-m-xylenol), triclosan (i.e., 2, 4, 4 '-trichloro-2' hydroxy-diphenylether), thymol, and triclocarban;

(vi) sunscreen actives including oxybenzone, octylmethoxy cinnamate, butylmethoxy dibenzoyln ethane, p-aminobenzoic acid and octyl dimethyl-p-aminobenzoic acid;

(vii) antioxidants such as beta-carotene, vitamin C (Ascorbic Acid) or an ester thereof, vitamin A or an ester thereof, vitamin E or an ester thereof, lutein or an ester thereof, lignan, lycopene, selenium, flavonoids, vitamin-like antioxidants such as coenzyme Q10 (CoQ10) and glutathione, and antioxidant enzymes such as superoxide dismutase (SOD), catalase, and glutathione peroxidase;

(viii) anti-inflammatory agents including, e.g., methyl salicylate, aspirin, ibuprofen, and naproxen. Additional anti-inflammatories useful in topical applications include corticosteroids, such as, but not limited to, flurandrenolide, clobetasol propionate, halobetasol propionate, fluticasone propionate, betamethasone dipropionate, betamethasone benzoate, betamethasone valerate, desoximethasone, dexamethasone, diflorasone diacetate, mometasone furoate, 1 amcinodine, halcinonide, fluocinonide, fluocinolone acetonide, desonide, triamcinolone acetonide, hydrocortisone, hydrocortisone acetate, fluoromethalone, methylprednisolone, and predinicarbate;

(ix) anesthetics that can be delivered locally including benzocaine, butamben, butamben picrate, cocaine, procaine, tetracaine, lidocaine and pramoxine hydrochloride;

(x) analgesics such as ibuprofen, diclofenac, capsaicin, and lidocaine;

(xi) antifungal agents. Non-limiting examples are micanazole, clotrimazole, butoconazole, fenticonasole, tioconazole, terconazole, sulconazole, fluconazole, haloprogin, ketonazole, ketoconazole, oxinazole, econazole, itraconazole, torbinafine, nystatin and griseofulvin;

(xii) antibiotics such as erythromycin, clindamycin, synthomycin, tetracycline, metronidazole and the like;

(xiii) anti-viral agents including famcyclovir, valacyclovir and acyclovir;

(xiv) anti-parasitic agents such as scabicedes, such as permethrin, crotamiton, lindane and ivermectin;

(xv) anti-infectious and anti-acne agents including benzoyl peroxide, sulfur, resorcinol and salicylic acid;

(xvi) dermatological active ingredients useful in topical applications including, e.g., jojoba oil and aromatic oils such as methyl salicylate, wintergreen, peppermint oil, bay oil, eucalyptus oil and citrus oils, as well as ammonium phenolsulfonate, bismuth subgallate, zinc phenolsulfonate and zinc salicylate;

(xvii) enzymes and co-enzymes useful for topical application including co-enzyme Q10, papain enzyme, lipases, proteases, superoxide dismutase, fibrinolysin, desoxyribonuclease, trypsin, collagenase and sutilains;

(xviii) skin whitening agents such as hydroquinone and monobenzone;

(xix) anti-histamines including chlorpheniramine, brompheniramine, dexchlorpheniramine, tripolidine, clemastine, diphenhydramine, prometazine, piperazines, piperidines, astemizole, loratadine and terfonadine;

(xx) chemotherapeutic agents such as 5-fluorouracil, masoprocol, mechlorethamine, cyclophosphamide, vincristine, chlorambucil, streptozocin, methotrexate, bleomycin, dactinomycin, daunorubicin, coxorubicin and tamoxifen;

(xxi) insect repellents including pediculicides for treatment of lice, such as pyrethrins, permethrin, malathion, lindane and the like (xxii) taste modulators including sweetness enhancer such as positive allosteric modulators (PAMs), bitterness inhibitors, saltiness enhancers, sourness inhibitors, and umami enhancers. Active materials also include flavor enhancer, taste modulators and artificial sweeteners. Exemplary sweetener and sweet modulators are rebaudioside C; plant extracts and derivatives, e.g., transglucosylated *R. suavissimus* extract; naringenin and salts; positive allosteric modulators ("PAMs") such as sulfamide compounds. See WO 2013/096290; US 2015/0305380; US 2015/0272184; and WO 2015/199987. Exemplary salt taste modulators include apsaicin; resiniferatoxin (RTX); piperine; 2-(3,4-dimethylbenzyl)-3-{[(4-hydroxy-3-methoxybenzyl)amino]carbothioyl}propyl pivalate (agonist 23); olvanil, capsiate; evodiamine; ethanol; cetylpyridinium chloride; dodecylpyridinium bromide; capsazepin; SB366791, etc. See WO 2005/006/881;

(xxiii) sweeteners such as steviol glycosides (Stevioside, Rebaudioside A, Rebaudioside C, Dulcoside A, Rebaudioside B, Rebaudioside D, Rebaudioside E, rubusoside, and combinations thereof), carbohydrate sweetener (sucrose, lactose, trehalose, glucose, fructose, sorbitol, mannitol, lactitol, xylitol, inulin, oligofructose, fructooligosaccharides, corn syrup, fruit juice concentrate, honey, malt, rice syrup, molasses, and agave syrup), and other artificial sweeteners (aspartame, sucralose, neotame, acesulfame potassium (Ace-K), saccharin, and advantame).

(xxxiv) probiotics, namely live microorganisms which, when administered in effective amounts, confer a beneficial physiological effect on the host. Examples include *L. bulgaricus, S. thermophiles, B. bifidum, L. lactis* spp. *Lactis, B. infantis, B. longum, L. paracasei, L. acidophilus, B. lactis, L. casei, B. adolescentis, B. breve, L. rhamnosus*, and other *Lactobacillus* and *Bifidobacterium* genera.

In addition to the active materials listed above, the products of this invention can also contain, for example, the following dyes, colorants or pigments: lactoflavin (riboflavin), beta-carotene, riboflavin-5'-phosphate, alpha-carotene, gamma-carotene, cantaxanthin, erythrosine, curcumin, quinoline yellow, yellow orange S, tartrazine, bixin, norbixin (annatto, orlean), capsanthin, capsorubin, lycopene, beta-apo-8'-carotenal, beta-apo-8'-carotenic acid ethyl ester, xantophylls (flavoxanthin, lutein, cryptoxanthin, rubixanthin, violaxanthin, rodoxanthin), fast carmine (carminic acid, cochineal), azorubin, cochineal red A (Ponceau 4 R), beetroot red, betanin, anthocyanins, amaranth, patent blue V, indigotine I (indigo-carmine), chlorophylls, copper compounds of chlorophylls, acid brilliant green BS (lissamine green), brilliant black BN, vegetable carbon, titanium dioxide, iron oxides and hydroxides, calcium carbonate, aluminum, silver, gold, pigment rubine BK (lithol rubine BK), methyl violet B, victoria blue R, victoria blue B, acilan brilliant blue FFR (brilliant wool blue FFR), naphthol green B, acilan fast green 10 G (alkali fast green 10 G), ceres yellow GRN, sudan blue II, ultramarine, phthalocyanine blue, phthalocayanine green, fast acid violet R. Further naturally obtained extracts (for example paprika extract, black carrot extract, red cabbage extract) can be used for coloring purposes. Goods results are also achieved with the colors named in the following, the so-called aluminum lakes: FD & C Yellow 5 Lake, FD & C Blue 2 Lake, FD & C Blue 1 Lake, Tartrazine Lake, Quinoline Yellow Lake, FD & C Yellow 6 Lake, FD & C Red 40 Lake, Sunset Yellow Lake, Carmoisine Lake, Amaranth Lake, Ponceau 4R Lake, Erythrosyne Lake, Red 2G Lake, Allura Red Lake, Patent Blue V Lake, Indigo Carmine Lake, Brilliant Blue Lake, Brown HT Lake, Black PN Lake, Green S Lake and mixtures thereof.

In some embodiments, the amount of encapsulated active material is from 0.5% to 80% (e.g., 5 to 65%, 15 to 55%, 20 to 45%, and 25 to 40%) by weight of the capsule slurry as prepared; and the amount of the capsule wall is from 0.5% to 25% (e.g., 1.5 to 15% and 2.5 to 10%) also by weight of the capsule slurry as prepared. In other embodiments, the amount of the encapsulated active material is from 15% to 99.5% (e.g., 50 to 98% and 30 to 95%) by weight of the capsule, and the amount of the capsule wall is from 0.5% to 85% (e.g., 2 to 50% and 5 to 70%) by weight of the capsule.

Deposition Aids

Deposition aids can also be used to assist the deposition of the delivery system to surfaces such as fabric, hair or skin. Examples include but are not limited to anionically, cationically, nonionically, or zwitterionically charged water-soluble polymers. These water-soluble polymers can also be amphoteric polymers with a ratio of cationic and anionic functionalities resulting in a net total charge of zero or positive, i.e., cationic. Those skilled in the art would appreciate that the charge of these polymers can be adjusted by changing the pH, depending on the product in which this technology is to be used. Any suitable method for coating the deposition aids onto the active material/delivery system can be used. The nature of suitable polymers for assisted delivery to interfaces depends on the compatibility with the delivery system chemistry since there has to be some association to the delivery system. This association can be through physical interactions, such as hydrogen bonding, ionic interactions, hydrophobic interactions, electron transfer interactions or, alternatively, chemical (covalent) bonding. The deposition polymer can be selected from one or more polymers with an overall zero (amphoteric: mixture of cationic and anionic functional groups) or net positive charge, based on the following polymer backbones: polysaccharides, polypeptides, polycarbonates, polyesters, polyolefinic (vinyl, acrylic, acrylamide, poly diene), polyester, polyether, polyurethane, polyoxazoline, polyamine, silicone, polyphosphazine, olyaromatic, poly heterocyclic, or polyionene, with molecular weight (MW) ranging from 1,000 to 1000,000,000 (e.g., 1,000 to 1,000,000, 10,000 to 500,000, 100,000 to 200,000, and 5,000 to 10,000,000). As used herein, molecular weight is provided as weight average molecular weight.

Examples of amphoteric and cationic polymers include, but not limited to, polyquaternium and polyvinylamine and its copolymers with vinylformamide and mixtures thereof. Polyquaternium includes polyquaternium-6 (poly(diallyldimethyl-ammonium chloride), commercially available from Lubrizol as MERQUAT 100), polyquaternium-22 (commercially available from Lubrizol as MERQUAT 280), polyquaternium-39 (commercially available from Lubrizol as MERQUAT 3330), polyquaternium-47 (a terpolymer of acrylic acid, methacrylamidopropyl trimethylammonium chloride, and methyl acrylate, commercially available as MERQUAT 2001), and polyquaternium-53 (copolymer of acrylic acid, acrylamide, methacrylamidopropyltrimonium chloride, commercially available as MERQUAT 2003PR). Polyvinylamines are polymers which are prepared by acidic or alkaline hydrolysis of poly(N-vinylformamides), as described, e.g., by Gu, et al. ((2002) *J. Appl. Pol. Sci.* 86:3412-3419). The corresponding products are produced in various molecular weights by BASF AG under the trade name "LUPAMIN". These products are used on a large scale, for example, as paper chemicals, in the personal care sector, as super-absorbents or dispersants. The LUPAMIN commercial products still contain the salts formed from the hydrolysis. For the application sector described, the modification of waveguide surfaces, both the salt-containing and the desalinified form can be used. The desalinification can be effected, for example, by ultrafiltration. In a preferred embodiment the polyvinylamine is LUPAMIN 9095 (polyvinylamine, average molecular weight 340,000 g/mol) commercially available from BASF. Polyethyleneimine are commercially available, e.g., Lupasol G20 and Lupasol SK, both by BASF.

Additional examples of cationic polymers include, e.g., polysaccharides such as guar, alginates, starch, xanthan, chitosan, cellulose, dextrans, arabic gum, carrageenan, and hyaluronates. These polysaccharides can be employed with cationic modification and alkoxy-cationic modifications such as cationic hydroxyethyl or cationic hydroxypropyl. For example, cationic reagents of choice are 3-chloro-2-hydroxypropyl trimethylammonium chloride or its epoxy version. Another example is graft-copolymers of polyDAD-MAC on cellulose, e.g., CELQUAT L-200 (POLYQUATERNIUM-4), POLYQUATERNIUM-10 and POLYQUATERNIUM-24, commercially available from National Starch, Bridgewater, NJ. Alternatively, polysaccharides can be employed with aldehyde, carboxyl, succinate, acetate, alkyl, amide, sulfonate, ethoxy, propoxy, butoxy, and combinations of these functionalities; or any hydrophobic modification (compared to the polarity of the polysaccharide backbone). The above modifications can be in any ratio and the degree of functionalization can be up to complete substitution of all functionalizable groups, as long as the theoretical net charge of the polymer is zero (mixture of cationic and anionic functional groups) or preferably positive. Furthermore, up to 5 different types of functional groups may be attached to the polysaccharides. Also, polymer graft chains may be differently modified to the backbone. The counterions can be any halide ion or organic counter ion. See U.S. Pat. Nos. 6,297,203 and 6,200,554.

Another source of cationic polymers contain protonatable amine groups so that the overall net charge is zero (amphoteric: mixture of cationic and anionic functional groups) or positive. The pH during use will determine the overall net charge of the polymer. Examples include silk protein, zein, gelatin, keratin, collagen and any polypeptide, such as polylysine.

Further cationic polymers include polyvinyl polymers with up to 5 different types of monomers can be used. The monomers of such polymer have the generic formula:

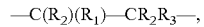

wherein, $R_1$ is a $C_1$-$C_{25}$ alkane or H, wherein the number of double bonds ranges from 0-5, $R_1$ is an alkoxylated fatty alcohol with any alkoxy carbon-length of $C_1$-$C_{25}$, or $R_1$ is a liquid crystalline moiety that can provide the polymer with thermotropic liquid crystalline properties;

$R_2$ is H or $CH_3$; and $R_3$ is —Cl, —$NH_2$ (i.e., polyvinyl amine or its copolymers with N-vinyl formamide.

Such polyvinyl polymers are sold under the name LUPAMIN 9095 by BASF Corporation. Further suitable cationic polymers containing hydroxylalkylvinylamine units, as disclosed in U.S. Pat. No. 6,057,404.

Another class of materials are polyacrylates with up to 5 different types of monomers. Monomers of polyacrylates have the generic formula:

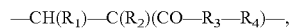

wherein, $R_1$ is a $C_1$-$C_{25}$ alkane from or H with a number of double bonds from 0-5, $R_1$ is an alkoxylated fatty alcohol with a $C_1$-$C_{25}$ alkyl chain length, or $R_1$ is a liquid crystalline moiety that provides the polymer with thermotropic liquid crystalline properties;

$R_2$ is H or $CH_3$;

$R_3$ is a $C_1$-$C_{25}$ alkyl alcohol or an alkylene oxide with any number of double bonds, or $R_3$ may be absent such that the C=O bond is (via the C-atom) directly connected to $R_4$; and $R_4$ can be —$NH_2$, —$NHR_1$, —$NR_1R_2$, —$NR_1R_2R_6$ (where $R_6$=$R_1$, $R_2$, or —$CH_2$—COOH or its salt), —NH—C(O)—, sulfobetaine, betaine, polyethylene oxide, poly(ethyleneoxide/propylene oxide/butylene oxide) grafts with any end group, H, OH, styrene sulfonate, pyridine, quaternized pyridine, alkyl-substituted pyrrolidone or pyridine, pyridine-N-oxide, imidazolinium halide, imidazolium halide, imidazol, piperidine, —$OR_1$, —OH, —COOH alkali salt, sulfonate, ethoxy sulphate, pyrrolidone, caprolactam, phenyl-$R_4$ or naphthalene-$R_5$, where $R_4$ and $R_5$ are $R_1$, $R_2$, $R_3$, sulfonic acid or its alkali salt or organic counter ion. Also, glyoxylated cationic polyacrylamides can be used. Typical polymers of choice are those containing the cationic monomer dimethylaminoethyl methacrylate (DMAEMA) or methacrylamidopropyl trimethyl ammonium chloride (MAPTAC). DMAEMA can be found in GAFQUAT and GAFFIX VC-713 polymers from ISP. MAPTAC can be found in BASF's LUVIQUAT PQ11 PN and ISP's GAFQUAT HS100.

Another group of polymers that can be used are those that contain cationic groups in the main chain or backbone. Included in this group are:
i) polyalkylene imines such as polyethylene imine, commercially available as LUPASOL from BASF. Any molecular weight and any degree of crosslinking of this polymer can be used in the present invention;
ii) ionenes as disclosed in U.S. Pat. Nos. 4,395,541 and 4,597,962;
iii) adipic acid/dimethyl amino hydroxypropyl diethylene triamine copolymers, such as CARTARETIN F-4 and F-23, commercially available from Sandoz;
iv) polymers of the general formula: —[N($CH_3$)$_2$—($CH_2$)$_x$—NH—(CO)—NH—($CH_2$)$_y$—N($CH_3$)$_2$)—($CH_2$)$_z$—O—(—$CH_2$)$_p$]$_n$—, with x, y, z, p=1-12, and n according to the molecular weight requirements. Examples are Polyquaternium 2 (MIRAPOL A-15), Polyquaternium-17 (MIRAPOL AD-1), and Polyquaternium-18 (MIRAPOL AZ-1). Other polymers include cationic polysiloxanes and cationic polysiloxanes with carbon-based grafts with a net theoretical positive charge or equal to zero (mixture of cationic and anionic functional groups). This includes cationic end-group functionalized silicones (i.e., Polyquaternium-80). Silicones with general structure: —Si($R_1$)($R_2$)—O-]$_x$-[Si($R_3$)($R_2$)—O-]$_y$— where $R_1$ is a $C_1$-$C_{25}$ alkane or H with the number of double bonds from 0-5, aromatic moieties, polysiloxane grafts, or mixtures thereof. $R_1$ can also be a liquid crystalline moiety that can provide the polymer with thermotropic liquid crystalline properties. $R_2$ can be H or $CH_3$; and $R_3$ can be —$R_1$—$R_4$, where $R_4$ can be —$NH_2$, —$NHR_1$, —$NR_1R_2$, —$NR_1R_2R_6$ (where $R_6$=$R_1$, $R_2$, or —$CH_2$—COOH or its salt), —NH—C(O)—, —COOH, —COO-alkali salt, any C1-25 alcohol, —C(O)—$NH_2$ (amide), —C(O)—N($R_2$) ($R_2$') ($R_2$"), sulfobetaine, betaine, polyethylene oxide, poly(ethyleneoxide/propylene oxide/butylene oxide) grafts with any end group, H, —OH, styrene sulfonate, pyridine, quaternized pyridine, alkyl-substituted pyrrolidone or pyridine, pyridine-N-oxide, imidazolinium halide, imidazolium halide, imidazol, piperidine, pyrrolidone, caprolactam, sulfonate, ethoxysulphate phenyl-$R_5$ or naphthalene-$R_6$ where $R_5$ and $R_6$ are $R_1$, $R_2$, $R_3$, sulfonic acid or its alkali salt or organic counter ion. $R_3$ can also be —($CH_2$)$_x$—O—$CH_2$—CH(OH)—$CH_2$—N($CH_3$)$_2$—$CH_2$—COOH and its salts. Any mixture of these $R_3$ groups can be selected. X and y can be varied as long as the theoretical net charge of the polymer is zero (amphoteric) or positive. In addition, polysiloxanes containing up to 5 different types of monomeric units may be used. Examples of suitable polysiloxanes are found in U.S. Pat. Nos. 4,395,541 4,597,962 and 6,200,554. Another group of polymers that can be used to improve capsule/particle deposition are phospholipids that are modified with cationic polysiloxanes. Examples of these polymers are found in U.S. Pat. No. 5,849,313, WO Patent Application 95/18096A1 and European Patent EP0737183B1.

Furthermore, copolymers of silicones and polysaccharides and proteins can be used (e.g., those commercially available as CRODASONE brand products).

Another class of polymers includes polyethylene oxide-co-propyleneoxide-co-butylene oxide polymers of any ethylene oxide/propylene oxide/butylene oxide ratio with cationic groups resulting in a net theoretical positive charge or equal to zero (amphoteric). Examples of such polymers are the commercially available TETRONIC brand polymers.

Suitable polyheterocyclic (the different molecules appearing in the backbone) polymers include the piperazine-alkylene main chain copolymers disclosed by Kashiki and Suzuki (1986) *Ind. Eng. Chem. Fundam.* 25:120-125.

In some embodiments, the composition contains from 0.01 to 20 weight percent of the deposition aid, on a solid basis. In other embodiments, the composition contains from 0.1 to 10 weight percent of the deposition aid.

Any compound, polymer, or agent discussed above can be the compound, polymer, or agent itself as shown above, or its salt, precursor, hydrate, or solvate. A salt can be formed between an anion and a positively charged group on the compound, polymer, or agent. Suitable anions include chloride, bromide, iodide, sulfate, nitrate, phosphate, citrate, methanesulfonate, trifluoroacetate, acetate, malate, tosylate, tartrate, fumarate, glutamate, glucuronate, lactate, glutarate, and maleate. Likewise, a salt can also be formed between a cation and a negatively charged group on the compound, polymer, or agent. Suitable cations include sodium ion, potassium ion, magnesium ion, calcium ion, and an ammonium cation (e.g., tetramethylammonium ion). A precursor can be ester and another suitable derivative, which, during the process of preparing a delivery system of this invention, is capable of converting to the compound, polymer, or agent and being used in preparing the delivery system. A hydrate refers to the compound, polymer, or agent that contains water. A solvate refers to a complex formed between the compound, polymer, or agent and a suitable solvent. A suitable solvent can be water, ethanol, isopropanol, ethyl acetate, acetic acid, and ethanolamine.

Certain compounds, polymers, and agents have one or more stereocenters, each of which can be in the R configuration, the S configuration, or a mixture. Further, some compounds, polymers, and agents possess one or more double bonds wherein each double bond exists in the E (trans) or Z (cis) configuration, or combinations thereof. The compounds, polymers, and agents include all possible configurational stereoisomeric, regioisomeric, diastereomeric, enantiomeric, and epimeric forms as well as any mixtures thereof.

Applications

The delivery system of the present invention are well-suited for use, without limitation, in the following products:
a) Household products
   i. Liquid or Powder Laundry Detergents which can use the present invention include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818
   ii. Unit Dose Pouches, Tablets and Capsules such as those described in EP 1 431 382 A1, US 2013/0219996 A1, US 2013/0284637 A1, and U.S. Pat. No. 6,492,315. These unit dose formulations can contain high concentrations of a functional material (e.g., 5-100% fabric softening agent or detergent active), fragrance (e.g., 0.5-100%, 0.5-40%, and 0.5-15%), and flavor (e.g., 0.1-100%, 0.1-40%, and 1-20%). They can contain no water to limit the water content as low as less than 30% (e.g., less than 20%, less than 10%, and less than 5%).
   iii. Scent Boosters such as those described in U.S. Pat. Nos. 7,867,968, 7,871,976, 8,333,289, US 2007/0269651 A1, and US2014/0107010 A1.
   iv. Fabric Care Products such as Rinse Conditioners (containing 1 to 30 weight % of a fabric conditioning active), Fabric Liquid Conditioners (containing 1 to 30 weight % of a fabric conditioning active), Tumble Drier Sheets, Fabric Refreshers, Fabric Refresher Sprays, Ironing Liquids, and Fabric Softener Systems such as those described in U.S. Pat. Nos. 6,335,315, 5,674,832, 5,759,990, 5,877,145, 5,574,179, 5,562,849, 5,545,350, 5,545,340, 5,411,671, 5,403,499, 5,288,417, 4,767,547 and 4,424,134
      Liquid fabric softeners/fresheners contains at least one fabric softening agent present, preferably at a concentration of 1 to 30% (e.g., 4 to 20%, 4 to 10%, and 8 to 15%). The ratio between the active material and the fabric softening agent can be 1:500 to 1:2 (e.g., 1:250 to 1:4 and 1:100 to 1:8). As an illustration, when the fabric softening agent is 5% by weight of the fabric softener, the active material is 0.01 to 2.5%, preferably 0.02 to 1.25% and more preferably 0.1 to 0.63%. As another example, when the fabric softening agent is 20% by weight of the fabric softener, the active material is 0.04 to 10%, preferably 0.08 to 5% and more preferably 0.4 to 2.5%. The active material is a fragrance, malodor counteractant or mixture thereof. The liquid fabric softener can have 0.15 to 15% of capsules (e.g., 0.5 to 10%, 0.7 to 5%, and 1 to 3%). When including capsules at these levels, the neat oil equivalent (NOE) in the softener is 0.05 to 5% (e.g., 0.15 to 3.2%, 0.25 to 2%, and 0.3 to 1%).
      Suitable fabric softening agents include cationic surfactants. Non-limiting examples are quaternary ammonium compounds such as alkylated quaternary ammonium compounds, ring or cyclic quaternary ammonium compounds, aromatic quaternary ammonium compounds, diquaternary ammonium compounds, alkoxylated quaternary ammonium compounds, amidoamine quaternary ammonium compounds, ester quaternary ammonium compounds, and mixtures thereof. Fabric softening compositions, and components thereof, are generally described in US 2004/0204337 and US 2003/0060390. Suitable softening agents include esterquats such as Rewoquat WE 18 commercially available from Evonik Industries and Stepantex SP-90 commercially available from Stepan Company.
   v. Liquid dish detergents such as those described in U.S. Pat. Nos. 6,069,122 and 5,990,065
   vi. Automatic Dish Detergents such as those described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562
   vii. All-purpose Cleaners including bucket dilutable cleaners and toilet cleaners
   viii. Bathroom Cleaners
   ix. Bath Tissue
   x. Rug Deodorizers
   xi. Candles
   xii. Room Deodorizers
   xiii. Floor Cleaners
   xiv. Disinfectants
   xv. Window Cleaners
   xvi. Garbage bags/trash can liners
   xvii. Air Fresheners including room deodorizer and car deodorizer, scented candles, sprays, scented oil air freshener, Automatic spray air freshener, and neutralizing gel beads
   xviii. Moisture absorber
   xix. Household Devices such as paper towels and disposable Wipes
   xx. Moth balls/traps/cakes
b) Baby Care Products
   i. Diaper Rash Cream/Balm
   ii. Baby Powder
c) Baby Care Devices
   i. Diapers
   ii. Bibs
   iii. Wipes
d) Oral Care Products. Tooth care products (as an example of preparations according to the invention used for oral care) generally include an abrasive system (abrasive or polishing agent), for example silicic acids, calcium carbonates, calcium phosphates, aluminum oxides and/or hydroxylapatites, surface-active substances, for example sodium lauryl sulfate, sodium lauryl sarcosinate and/or cocamidopropylbetaine, humectants, for example glycerol and/or sorbitol, thickening agents, for example carboxymethyl cellulose, polyethylene glycols, carrageenan and/or Laponite®, sweeteners, for example saccharin, taste correctors for unpleasant taste sensations, taste correctors for further, normally not unpleasant taste sensations, taste-modulating substances (for example inositol phosphate, nucleotides such as guanosine monophosphate, adenosine monophosphate or other substances such as sodium glutamate or 2-phenoxypropionic acid), cooling active ingredients, for example menthol derivatives, (for example L-menthyllactate, L-menthylalkylcarbonates, menthone ketals, menthane carboxylic acid amides), 2,2,2-trialkylacetic acid amides (for example 2,2-diisopropylpropionic acid methyl amide), icilin and icilin derivatives, stabilizers and active ingredients, for example sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan, cetylpyridinium chloride, aluminum lactate, potassium citrate, potassium nitrate, potassium chloride, strontium chloride, hydrogen peroxide, flavorings and/or sodium bicarbonate or taste correctors.
  i. Tooth Paste. An exemplary formulation as follows:
    1. calcium phosphate 40-55%
    2. carboxymethyl cellulose 0.8-1.2%
    3. sodium lauryl sulfate 1.5-2.5%
    4. glycerol 20-30%
    5. saccharin 0.1-0.3%
    6. flavor oil 1.0-2.5%
    7. water q.s. to 100%
      A typical procedure for preparing the formulation includes the steps of (i) mixing by a blender according to the foregoing formulation to provide a toothpaste, and (ii) adding a composition of this invention and blending the resultant mixture till homogeneous.
  iii. Oral Rinse
  ii. Tooth Powder
  iv. Tooth Whiteners
  v. Denture Adhesive
e) Health Care Devices
  i. Dental Floss
  ii. Toothbrushes
  iii. Respirators
  iv. Scented/flavored condoms
f) Feminine Hygiene Products such as Tampons, Feminine Napkins and Wipes, and Pantiliners
g) Personal Care Products: Cosmetic or pharmaceutical preparations, e.g., a "water-in-oil" (W/O) type emulsion, an "oil-in-water" (O/W) type emulsion or as multiple emulsions, for example of the water-in-oil-in-water (W/O/W) type, as a PIT emulsion, a Pickering emulsion, a micro-emulsion or nano-emulsion; and emulsions which are particularly preferred are of the "oil-in-water" (O/W) type or water-in-oil-in-water (W/O/W) type. More specifically,
  i. Personal Cleansers (bar soaps, body washes, and shower gels)
  ii. In-shower conditioner
  iii. Sunscreen ant tattoo color protection (sprays, lotions, and sticks)
  iv. Insect repellants
  v. Hand Sanitizer
  vi. Antiinflammatory balms, ointments, and sprays
  vii. Antibacterial ointments and creams
  viii. Sensates
  ix. Deodorants and Antiperspirants including aerosol and pump spray antiperspirant, stick antiperspirant, roll-on antiperspirant, emulsion spray antiperspirant, clear emulsion stick antiperspirant, soft solid antiperspirant, emulsion roll-on antiperspirant, clear emulsion stick antiperspirant, opaque emulsion stick antiperspirant, clear gel antiperspirant, clear stick deodorant, gel deodorant, spray deodorant, roll-on, and cream deodorant.
  x. Wax-based Deodorant. An exemplary formulation as follows:
    1. Parafin Wax 10-20%
    2. Hydrocarbon Wax 5-10%
    3. White Petrolatum 210-15%
    4. Acetylated Lanolin Alcohol 2-4%
    5. Diisopropyl Adipate 4-8%
    6. Mineral Oil 40-60%
    7. Preservative (as needed)
      The formulation is prepared by (i) mixing the above ingredients, (ii) heating the resultant composition to 75° C. until melted, (iii) with stirring, adding 4% cryogenically ground polymer containing a fragrance while maintaining the temperature 75° C., and (iv) stirring the resulting mixture in order to ensure a uniform suspension while a composition of this invention is added to the formulation.
  xi. Glycol/Soap Type Deodorant. An exemplary formulation as follows:
    1. Propylene Glycol 60-70%
    2. Sodium Stearate 5-10%
    3. Distilled Water 20-30%
    4. 2,4,4-Trichloro-2'-Hydroxy Diphenyl Ether, manufactured by the Ciba-Geigy Chemical Company and a Trademark of the Ciba-Geigy Chemical Company) 0.01-0.5%
      The ingredients are combined and heated to 75° C. with stirring until the sodium stearate has dissolved. The resulting mixture is cooled to 40° C. followed by addition of a composition of this invention.
  xii. Lotion including body lotion, facial lotion, and hand lotion
  xiii. Body powder and foot powder
  xiv. Toiletries
  xv. Body Spray
  xvi. Shave cream and male grooming products
  xvii. Bath Soak
  xviii. Exfoliating Scrub
h) Personal Care Devices
  i. Facial Tissues
  ii. Cleansing wipes
i) Hair Care Products
  i. Shampoos (liquid and dry powder)
  ii. Hair Conditioners (Rinse-out conditioners, leave-in conditioners, and cleansing conditioners)
  iii. Hair Rinses
  iv. Hair Refreshers
  v. Hair perfumes
  vi. Hair straightening products
  vii. Hair styling products, Hair Fixative and styling aids
  viii. Hair combing creams
  ix. Hair wax
  x. Hair foam, hair gel, nonaerosol pump spray
  xi. Hair Bleaches, Dyes and Colorants
  xii. Perming agents
  xiii. Hair wipes
j) Beauty Care
  i. Fine Fragrance-Alcoholic. Compositions and methods for incorporating fragrance capsules into alcoholic fine fragrances are described in U.S. Pat. No. 4,428,869. Alcoholic fine fragrances may contain the following:
    1. Ethanol (1-99%)
    2. Water (0-99%)
    3. A suspending aide including but not limited to: hydroxypropyl cellulose, ethyl cellulose, silica, microcrystalline cellulose, carrageenan, propylene glycol alginate, methyl cellulose, sodium carboxymethyl cellulose or xanthan gum (0.-1-%)
4. Optionally an emulsifier or an emollient may be included including but not limited to those listed above
ii. Solid Perfume
iii. Lipstick/lip balm
iv. Make-up cleanser
v. Skin care cosmetic such as foundation, pack, sunscreen, skin lotion, milky lotion, skin cream, emollients, skin whitening
vi. Make-up cosmetic including manicure, mascara, eyeliner, eye shadow, liquid foundation, powder foundation, lipstick and cheek rouge
k) Consumer goods packaging such as fragranced cartons, fragranced plastic bottles/boxes
l) Pet care products
  i. Cat litter
  ii. Flea and tick treatment products
  iii. Pet grooming products
  iv. Pet shampoos
  v. Pet toys, treats, and chewables
  vi. Pet training pads
  vii. Pet carriers and crates
m) Confectionaries confectionery, preferably selected from the group consisting of chocolate, chocolate bar products, other products in bar form, fruit gums, hard and soft caramels and chewing gum
  i. Gum
    1. Gum base (natural latex chicle gum, most current chewing gum bases also presently include elastomers, such as polyvinylacetate (PVA), polyethylene, (low or medium molecular weight) polyisobutene (PIB), polybutadiene, isobutene-isoprene copolymers (butyl rubber), polyvinylethylether (PVE), polyvinylbutyether, copolymers of vinyl esters and vinyl ethers, styrene-butadiene copolymers (styrene-butadiene rubber, SBR), or vinyl elastomers, for example based on vinylacetate/vinyllaurate, vinylacetate/vinylstearate or ethylene/vinylacetate, as well as mixtures of the mentioned elastomers, as described for example in EP 0 242 325, U.S. Pat. Nos. 4,518,615, 5,093,136, 5,266,336, 5,601,858 or U.S. Pat. No. 6,986,709.) 20-25%
    2. Powdered sugar 45-50%
    3. glucose 15-17%
    4. starch syrup 10-13%
    5. plasticizer 0.1%
    6. flavor 0.8-1.2%
    The components described above were kneaded by a kneader according to the foregoing formulation to provide a chewing gum. Encapsulated Flavor or sensate is then added and blended till homogeneous.
  ii. Breath Fresheners
  iii. Orally Dissolvable Strips
  iv. Chewable Candy
  v. Hard Candy
n) Baked products, preferably selected from the group consisting of bread, dry biscuits, cakes and other cookies;
o) snack foods, preferably selected from the group consisting of baked or fried potato chips or potato dough products, bread dough products and corn or peanut-based extrudates;
  i. Potato, tortilla, vegetable or multigrain chips
  ii. Popcorn
  iii. Pretzels
  iv. Extruded stacks
p) Cereal Products preferably selected from the group consisting of breakfast cereals, muesli bars and precooked finished rice products
q) Alcoholic and non-alcoholic beverages, preferably selected from the group consisting of coffee, tea, wine, beverages containing wine, beer, beverages containing beer, liqueurs, schnapps, brandies, sodas containing fruit, isotonic beverages, soft drinks, nectars, fruit and vegetable juices and fruit or vegetable preparations; instant beverages, preferably selected from the group consisting of instant cocoa beverages, instant tea beverages and instant coffee beverages
  i. Ready to drink liquid drinks
  ii. Liquid Drink Concentrates
  iii. Powder Drinks
  iv. Coffee: Instant Cappucino
    1. Sugar 30-40%
    2. Milk Powder 24-35%
    3. Soluble Coffee 20-25%
    4. Lactose 1-=15%
    5. Food Grade Emulsifier 1-3%
    6. Encapsulated Volatile Flavor 0.01-0.5%
  v. Tea
  vi. Alcoholic
r) Spice blends and consumer prepared foods
  i. Powder gravy, sauce mixes
  ii. Condiments
  iii. Fermented Products
s) Ready to heat foods: ready meals and soups, preferably selected from the group consisting of powdered soups, instant soups, precooked soups
  i. Soups
  ii. Sauces
  iii. Stews
  iv. Frozen entrees
t) Dairy Products milk products, preferably selected from the group consisting of milk beverages, ice milk, yogurt, kefir, cream cheese, soft cheese, hard cheese, powdered milk, whey, butter, buttermilk and partially or fully hydrolyzed milk protein-containing products Flavored milk beverages
  i. Yoghurt
  ii. Ice cream
  iii. Bean Curd
  iv. Cheese
u) Soya protein or other soybean fractions, preferably selected from the group consisting of soya milk and products produced therefrom, soya lecithin-containing preparations, fermented products such as tofu or tempeh or products produced therefrom and soy sauces;
v) Meat products, preferably selected from the group consisting of ham, fresh or raw sausage preparations, and seasoned or marinated fresh or salt meat products
w) Eggs or egg products, preferably selected from the group consisting of dried egg, egg white and egg yolk
x) Oil-based products or emulsions thereof, preferably selected from the group consisting of mayonnaise, remoulade, dressings and seasoning preparations
y) fruit preparations, preferably selected from the group consisting of jams, sorbets, fruit sauces and fruit fillings; vegetable preparations, preferably selected from the group consisting of ketchup, sauces, dried vegetables, deep-frozen vegetables, precooked vegetables, vegetables in vinegar and preserved vegetables z) Flavored pet foods.

The above-listed applications are all well known in the art. For example, fabric softener systems are described in U.S. Pat. Nos. 6,335,315, 5,674,832, 5,759,990, 5,877,145, 5,574,179; 5,562,849, 5,545,350, 5,545,340, 5,411,671, 5,403,499, 5,288,417, and 4,767,547, 4,424,134. Liquid laundry detergents include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818. Liquid dish detergents are described in U.S. Pat. Nos. 6,069,122 and 5,990,065. Shampoo and conditioners that can employ the present invention include those described in U.S. Pat. Nos. 6,162,423, 5,968,286, 5,935,561, 5,932,203, 5,837,661, 5,776,443, 5,756,436, 5,661,118, 5,618,523, 5,275,755, 5,085,857, 4,673,568, 4,387,090 and 4,705,681. Automatic Dish Detergents are described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562.

All parts, percentages and proportions refer to herein and in the claims are by weight unless otherwise indicated.

The values and dimensions disclosed herein are not to be understood as being strictly limited to the exact numerical values recited. Instead, unless otherwise specified, each such value is intended to mean both the recited value and a functionally equivalent range surrounding that value. For example, a value disclosed as "50%" is intended to mean "about 50%."

As used herein, the terms "three-dimensional printing system," "three-dimensional printer," "3D printing system," and "3D printer" are used interchangeably and refer to any known 3D printing system or printer.

The term "polymer" includes oligomers having 2-10 repeated units and macromolecules having 11 or more repeated units.

The term "water-dissoluble" describes a polymer capable of being dissolved, loosened, disconnected, or dissociated in water so that the active material enclosed therein is released.

The invention is described in greater detail by the following non-limiting examples.

EXAMPLE 1

A cylindrical delivery system of this invention, i.e., Sample 1, was prepared following the procedure described below.

A 3D model was first built using 123Design, a CAD software commercially available from Autodesk Inc. The model was then saved as an .STL file that was consequently "sliced" on Makerbot's software (Makerware).

In the 123Design application, two cylinders having dimensions of 20 mm and 10 mm on Makerware software were created separately and then fused to model a delivery system using the Makerware software to slice and control processing parameter of the 3D printer, i.e., Replicator 2× having two printer heads (a fused deposition modeling system commercially available from Makerbot, New York, USA).

Sample 1 had a fragranced core and an unfragranced outer layer encapsulating the fragranced core. The outer layer is formed of a water-dissolvable polyvinyl alcohol (PVOH) by extruding from one of the two printer heads at 205° C. The core is formed of a mixture of polyethylene PolyIFF (commercially available from International Flavors and Fragrances, Union Beach, New Jersey) and polylactic acid at the weight ratio of 20/80 by extruding from the other printer head at 220° C. The thus prepared Sample 1 contained 1% fragrance.

EXAMPLE 2

Following the same procedure described in Example 1 above, a second delivery system, i.e., Sample 2, was designed as a spherical model having an outer layer and a core.

The printed product Sample 2 had a fragranced core (ID 10 mm) formed of a mixture of a fragranced polymer (i.e., polyethylene PolyIFF) and an unfragranced polymer (i.e., ABS, commercially available from Stratasys, Eden Prairie, MN) and an outer layer (ID 20 mm) formed of ABS. The outer layer encapsulated the fragranced core.

EXAMPLE 3

Following the same procedure described in Example 1 above, a third delivery system, i.e., Sample 3, was designed as a sheet-like model having three layers. Each layer had a thickness of 0.3 mm.

The printed product Sample 3 had a first and second outer layers (each had a thickness of 0.3 mm) formed of an unfragranced polymer (PVOH, commercially available from MakerBot, Brooklyn, NY), and an inner layer (thickness of 0.3 mm) formed of a fragranced polymer, which was polyethylene PolyIFF polymer filament prepared from pellets using a single screw extruder (CW Brabender) with a rod die. The filament had a diameter of 1.75 mm.

Sample 3 had a fragranced center layer, a first outer layer, and a second outer layer. The first and second layers together encapsulated the fragranced center layer. Each of the first and second outer layers is formed of a water-dissolvable polyvinyl alcohol (PVOH) by extruding from one of the two printer heads at 205° C. The center layer is formed of a mixture of PolyIFF and polylactic acid at the ratio of 20/80 by extruding from the other printer head at 220° C.

EXAMPLE 4

This example illustrates a process of preparing "micropackages" using lamination films. It is preferred that the process use ambient temperature in order to protect the active material from heat loss or degradation. The active material may be in the form of a powder, granule, liquid, or a combination thereof. One challenge is the ability to accurately deposit micrograms to milligrams of the active material onto the lamination film.

Sample 4 was prepared following the procedure described below.

MonoSol Film A200 (polyvinyl alcohol commercially available from Kuraray America, Houston, TX; having a thickness of 20 microns) was laminated using a desktop laminating machine to convert two sheets of the film into a fused film having a thickness of 40 microns. Before the lamination, a fine layer of a flavor powder (i.e., Raspberry IFFtru2Nature commercially available from International Flavors and Fragrances, Union Beach, New Jersey; 25% flavor load) was deposited to a first film. A second film was used to cover the first film and the deposited flavor powder. Both films were then laminated to fuse together to obtain Sample 4.

EXAMPLE 5

Sample 5 was prepared following the procedure described in Example 5 except that the films were fused together by wetting the surface of the films with the water in order to partially melt and thus fuse both films. No desktop laminating machine was used.

EXAMPLES 6 AND 7

Samples 6 and 7 were prepared to enclosing an oil in a lamination film.

More specifically, a first MonoSol Film A200 was embossed to create wells. A flavor oil, i.e., orange oil, thickened using Aerosil 200 fumed silica, was deposited into the wells. A second film was placed on top of the first film. Both films were fused together using adhesive to obtain Sample 6.

Sample 7 was prepared following the same procedure except that a fragrance oil (i.e., Greenfields commercially available from International Flavors and Fragrances, Union Beach, New Jersey), instead of orange oil, was used.

EXAMPLE 8

Sample 1 prepared above was tested for their release in water. More specifically, one piece of the delivery system was added to 5 mL of water in a 20 mL vial. A headspace analysis using a gas chromatograph was performed at two time points: time 0 and 5 hours after Sample 1 was added to water.

The chromatogram of the sample at time 0 showed no fragrance. The chromatogram at time 5 hours showed fragrance released from the delivery system, at which time the PVOH shell was dissolved in water.

EXAMPLE 9

Stability Experiments on Samples 4, 6 and 7 were conducted following the procedure described below.

More specifically, each sample was submerged in propylene glycol and kept in a closed jar at room temperature for observation.

Sample 4 remained fused after at least 11 days. A control sample was also set up in propylene glycol having the same flavor powder and the first film but without a second film. After 11 days, the control sample had a noticeably stronger raspberry aroma. The sealed film had a slight raspberry aroma and noticeably less intense than the control indicating reduced dissolution of the sealed flavor powder into the propylene glycol.

Samples 6 and 7 remained fused after at least 5 days. When the jars were opened, only a slight aroma characteristic of the flavor or fragrance was observed. This indicates that the film provided controlled release of the flavor or fragrance in propylene glycol.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Indeed, to prepare an effective delivery system, one skilled in the art can select a suitable polymer, active material, and structural design. Further, the thickness of each layers, the number of the layers, and the content of the active materials can also be determined by a skilled artisan through assays known in the art to prepare delivery systems with desirable properties.

From the above description, a skilled artisan can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of preparing a delivery system, the method comprising:
    (a) providing a first film,
    (b) depositing an active material to one or more predetermined areas on the first film with a printer head,
    (c) covering the active material and the first film with a second film,
    (d) bonding the first and second films thereby sealing the active material between the first and second films to obtain the delivery system,
    wherein each of the first and second films has a thickness of 10 to 100 micrometers, the active material, as a powder or oil, is a flavor, fragrance, malodor counteracting agent, or combination thereof, and
    wherein the printer head deposits between a microgram and milligram of the active material at the one or more predetermined areas on the first film.

2. The method of claim 1, wherein each of the first and second films is formed of an edible material and the active material is a flavor.

3. The method of claim 1, wherein each of the first and second films is formed of polyvinyl alcohol.

\* \* \* \* \*